(12) United States Patent
Olivier et al.

(10) Patent No.: US 7,195,354 B2
(45) Date of Patent: Mar. 27, 2007

(54) ADAPTIVE OPHTHALMOLOGIC SYSTEM

(75) Inventors: Scot S. Olivier, Livermore, CA (US);
Charles A. Thompson, Livermore, CA (US); Brian J. Bauman, Fremont, CA (US); Steve M. Jones, Livermore, CA (US); Don T. Gavel, Santa Cruz, CA (US); Abdul A. S. Awwal, Pleasanton, CA (US); Stephen K. Eisenbies, Pleasanton, CA (US); Steven J. Haney, Tracy, CA (US)

(73) Assignee: The Regents of The University of California, Oakland, CA (US)

( * ) Notice: Subject to any disclaimer, the term of this patent is extended or adjusted under 35 U.S.C. 154(b) by 576 days.

(21) Appl. No.: 10/674,891

(22) Filed: Sep. 29, 2003

(65) Prior Publication Data

US 2004/0100619 A1    May 27, 2004

Related U.S. Application Data

(60) Provisional application No. 60/416,197, filed on Oct. 4, 2002.

(51) Int. Cl.
*A61B 3/10* (2006.01)
(52) U.S. Cl. .......................... 351/205; 351/221
(58) Field of Classification Search .............. 351/200, 351/205, 211, 212, 221, 246
See application file for complete search history.

(56) References Cited

U.S. PATENT DOCUMENTS

| | | | |
|---|---|---|---|
| 5,777,719 A | 7/1998 | Williams et al. | |
| 6,338,559 B1 | 1/2002 | Williams et al. | |
| 6,379,005 B1 | 4/2002 | Williams et al. | |
| 6,511,180 B2* | 1/2003 | Guirao et al. | 351/211 |
| 6,761,454 B2* | 7/2004 | Lai et al. | 351/216 |
| 6,827,442 B2* | 12/2004 | Ross et al. | 351/205 |
| 6,871,951 B2* | 3/2005 | Blum et al. | 351/159 |
| 2002/0047992 A1 | 4/2002 | Graves et al. | |
| 2002/0140899 A1* | 10/2002 | Blum et al. | 351/159 |
| 2002/0140902 A1 | 10/2002 | Guirao et al. | |
| 2002/0180931 A1 | 12/2002 | Dick et al. | |

FOREIGN PATENT DOCUMENTS

| | | |
|---|---|---|
| WO | WO 01/58339 A2 | 8/2001 |
| WO | WO 02/24060 A1 | 3/2002 |
| WO | WO 02/30273 A1 | 4/2002 |
| WO | WO 02/46801 A2 | 6/2002 |
| WO | WO 03/034909 A2 | 5/2003 |

OTHER PUBLICATIONS

Wilks, S. C., et al., "High-Resolution Adaptive Optics Test-Bed for Vision Science," Adaptive Optics Systems and Technology II, Proceedings of SPIE vol. 4494, (2002), pp. 349-356.

* cited by examiner

*Primary Examiner*—Scott J. Sugarman
(74) *Attorney, Agent, or Firm*—Eddie E. Scott; John H. Lee

(57) ABSTRACT

A system for improving vision that can diagnose monochromatic aberrations within a subject's eyes, apply the wavefront correction, and then enable the patient to view the results of the correction. The system utilizes a laser for producing a beam of light; a corrector; a wavefront sensor; a testing unit; an optic device for directing the beam of light to the corrector, to the retina, from the retina to the wavefront sensor, and to the testing unit; and a computer operatively connected to the wavefront sensor and the corrector.

25 Claims, 3 Drawing Sheets

ADAPTIVE OPHTHALMOLOGIC SYSTEM

CROSS-REFERENCE TO RELATED APPLICATIONS

This application claims the benefit of U.S. Provisional Patent Application No. 60/416,197 filed Oct. 4, 2002 and titled "Adaptive Phoropter." U.S. Provisional Patent Application No. 60/416,197 filed Oct. 4, 2002 and titled Adaptive Phoropter is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to a method and apparatus for improving vision and more particularly to an adaptive ophthalmologic system.

2. State of Technology

U.S. Pat. No. 5,777,719 issued Jul. 7, 1998 to David R. Williams and Junzhong Liang, assigned to the University of Rochester, for a method and apparatus for improving vision and the resolution of retinal images provides the following state of technology information, "a point source produced on the retina of a living eye by a laser beam is reflected from the retina and received at a lenslet array of a Hartmann-Shack wavefront sensor such that each of the lenslets in the lenslet array forms an aerial image of the retinal point source on a CCD camera located adjacent to the lenslet array. The output signal from the CCD camera is acquired by a computer which processes the signal and produces a correction signal which may be used to control a compensating optical or wavefront compensation device such as a deformable mirror. It may also be used to fabricate a contact lens or intraocular lens, or to guide a surgical procedure to correct the aberrations of the eye. Any of these methods could correct aberrations beyond defocus and astigmatism, allowing improved vision and improved imaging of the inside of the eye."

U.S. Pat. No. 6,338,559 issued Jan. 15, 2002 to David R. Williams, Geun-Young Yoon, and Antonio Guirao, assigned to the University of Rochester, for an apparatus and method for improving vision and retinal imaging provides the following state of technology information, "A method for improving the visual performance of a person involves correcting higher-order monochromatic aberrations in combination with the correction of chromatic aberration. Such correction results in a visual benefit greater than that realized by correcting only the higher-order monochromatic aberrations or the chromatic aberration alone. The higher-order monochromatic aberrations are corrected by introducing appropriate phase profiles to compensate for the wavefront aberrations of the eye. This compensation can be provided by contact lenses, IOLs, inlays and onlays having appropriate surface shapes or by corneal shaping achieved through refractive surgery or other techniques. Chromatic aberration can be corrected by spectral filtering or artificial apodization. An apodization filter is described that provides a non-uniform amplitude transmission across the pupil of the eye. Contact lenses or other ocular devices for correcting higher-order monochromatic aberrations may include an appropriate apodization filter for correcting chromatic aberration, or an external optical device for correcting chromatic aberration may be used in combination with a contact lens, etc. for correcting the higher-order monochromatic aberrations."

International Patent Publication No. WO 02/30273 published Apr. 18, 2001 by the University of Rochester, inventors David R. Williams and Antonio Guirao, for determination of ocular refraction from wavefront aberration data provides the following state of technology information, "Ocular refraction is determined from wavefront aberration data, and an optimum customized correction is designed. The eye's wave aberration is measured (202) by using a detector such as a Shack-Hartmann detector (714). From the aberration, an image metric is calculated (214), and the second-order aberrations which optimize that metric are determined (218). From that optimization, the refractive correction (220) required for the eye is determined. The image metric is one of several metrics indicating the quality of the image on the retinal plane or a proxy for such a metric. The required refractive correction (220) can be used to form a lens or to control eye surgery. If it is possible to detect more aberrations than can be corrected, those aberrations are corrected which most affect vision, or for which the eye's error tolerance is lowest."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a method and apparatus for improving vision that can diagnose monochromatic aberrations within a subject's eyes, apply the wavefront correction, and then enable the patient to view the results of the correction. The present invention provides correction of higher order aberrations, i.e. corrections beyond defocus and astigmatism. The present invention integrates a modular wavefront sensor and analyzer. The system of the present invention is more stable, can be more readily aligned, and is more compact than existing systems. The system of the present invention is more clinically robust than existing systems and can be readily transported. The system of the present invention can be operated in both an open and a closed loop mode.

One embodiment of the present invention provides an apparatus for improving vision utilizing a patient's retina. The apparatus comprises a laser or other light source, such as a light emitting diode or super-luminescent diode, etc. for producing a beam of light; a corrector; a wavefront sensor; a testing unit; optic means for directing the beam of light to the corrector, to the retina, from the retina to the wavefront sensor, and to the testing unit; and a computer operatively connected to the wavefront sensor and the corrector.

Another embodiment of the present invention provides method of improving vision utilizing a patient's retina. The method comprising the steps of producing a beam of light utilizing a laser or other light source, directing the beam of light to a corrector, directing the beam of light from the corrector to the retina and producing a return beam of light, directing the return beam of light to the corrector, to a wavefront sensor, and to a testing unit.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
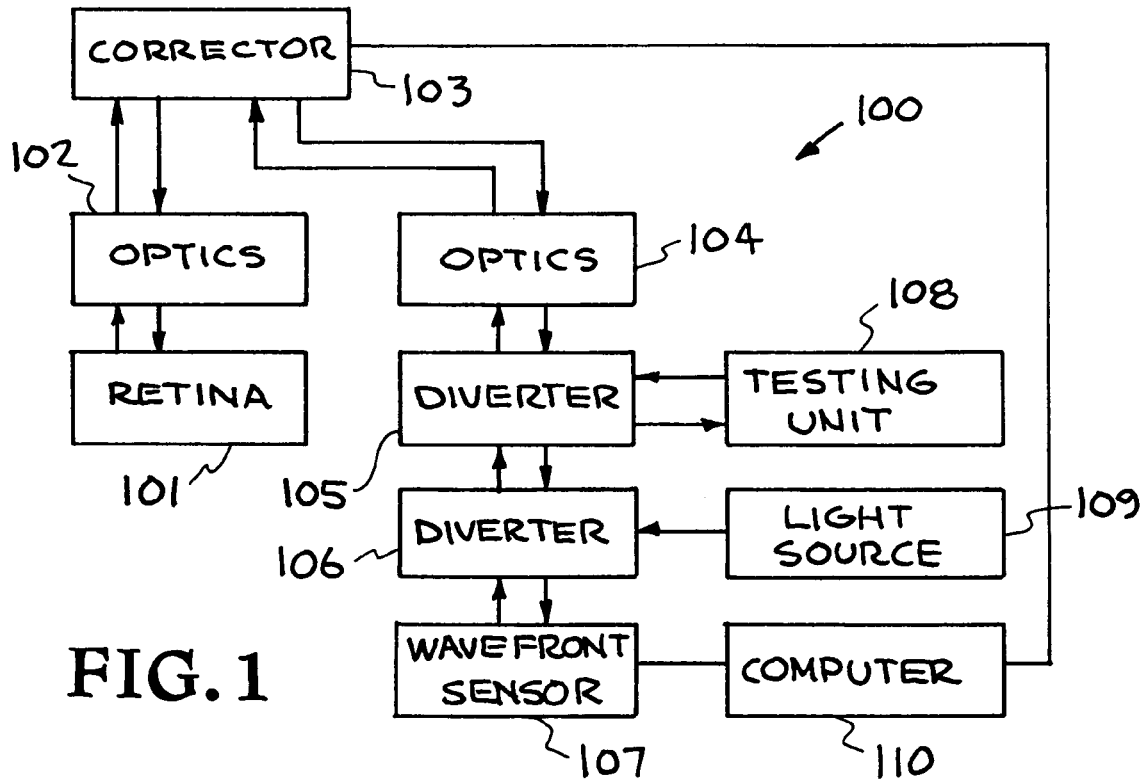
FIG. 1 illustrates an embodiment of a system constructed in accordance with the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The standard methods for vision correction, e.g., spectacles and contact lens, are only able to correct defocus and astigmatism. Higher order aberrations, such as spherical aberrations and coma, cannot be corrected using these devices. These higher order aberrations degrade vision, even after focus and astigmatism have been corrected using convention means. In addition, these aberrations impair the ability to image the human retina. Methods that correct for higher order aberrations could significantly improve the vision of patients and would also be useful in the diagnosis and treatment of ophthalmic diseases and conditions. Another major weakness is that traditional clinical methods rely heavily on the subjective opinion of clinicians. It would be highly desirable to quantitatively capture the wave aberration of the eye, apply a correction and then examine the result.

For years, optometrists and ophthalmologists have been using the phoropter to diagnose their patients' vision problems and specify their prescriptions for vision correction. FIG. 1 illustrates an embodiment of a system constructed in accordance with the present invention for improving the vision and resolution of retinal images. The system is designated generally by the reference numeral 100. The system 100 will enable clinicians to perform detailed vision assessments, apply the appropriate higher-order optical corrections, and then immediately present corrected images to their patients for confirmation. The system 100 will significantly improve the quality of vision corrections, particularly for those patients with elevated levels of higher-order aberrations, such as coma or spherical aberrations. The system 100 can enhance the quality of life for millions of people—including those seeking improved vision through laser eye surgery and, ultimately, those fighting vision loss and blindness caused by retinal diseases. The system 100 improves a patient's vision by directing a beam of light to the patient's retina 101. The system 100 comprises a number of operatively connected elements. The elements shown in FIG. 1 include optics 102, corrector 103, optics 104, diverter 105, diverter 106, wavefront sensor 107, testing unit 108, light source 109, and computer 110.

The light source 109 for example can be a laser, a light emitting diode, or a super-luminescent diode available from Wavefront Sciences, Inc., 14810 Central Ave. SE, Albuquerque, N.Mex. 87123. The diverters 105 and 106 for example can be "beam splitters available from Wavefront Sciences, Inc., 14810 Central Ave. SE, Albuquerque, N.Mex. 87123," "dog-legs," "flip in mirrors," or other "means for diverting light." The optics 102 and 104 for example can be a "telescopic lens," an "adjustable lens," a "phoropter available from Reichert Inc., 3374 Walden Avenue Depew, N.Y. 14043" or a combination of the foregoing. The corrector 103 for example can be a "deformable mirror," a "MEMS device," a "liquid crystal spatial light modulator," or a "MEMS deformable mirror available from Boston Micromachines Corporation, 108 Water Street, Watertown, Mass. 02472." The wavefront sensor 107 for example can be a "Hartmann-Shack type wavefront sensor," a "Hartmann-Shack sensor as described in WO 02/34126, WO 01/58339, WO 02/46801, U.S. Pat. No. 6,382,793, or WO 02/24060, which are incorporated herein by reference)," or a "wavefront sensor available from Wavefront Sciences, Inc., 14810 Central Ave. SE, Albuquerque, N.Mex. 87123." The testing unit 108 for example can be an "eye chart" or "other means for testing the eye." In various embodiments the testing unit includes an eye chart, a video projector, a video monitor, or other testing unit. The computer 110 for example can be a "general purpose computer."

Now that the various elements of the system 100 have been identified and described, the operation of the system 100 will be considered. Light is generated and introduced into the system by the light source 109. The light passes through diverter 106, diverter 105, and optics 104 to corrector 103. The light passes from the corrector 103 through the optics 102 to the retina 101. In various embodiments the corrector comprises a microelectromechanical system corrector, a deformable mirror, a liquid crystal spatial light modulator, and a microelectromechanical system deformable mirror. The light creates an image on the retina 101. The return light with the image passes from retina 101 through the optics 102 to the corrector 103. The return light passes from the corrector 103 through the optics 104, diverter 105, and diverter 106, to the wavefront sensor 109. The return light signal from the wavefront sensor 109 is directed to the computer 110. The computer 110 is connected to the corrector 103. The return light also passes from the corrector 103 through optics 104 and diverter 105 to the testing unit 108.

The corrector 103 will apply the appropriate correction, automatically calculated by the wavefront sensor 107 and computer 110. This information is combined with the response from the patient, so that the clinician and patient, can attain the best correction and compensate for high-order aberrations.

Patients will have nearly the same experience as they have today. They will view a visual scene (e.g., an eye chart) and asked to comment on whether the scene appears clearer. The clinicians' experience will also be similar, except they will not need to perform many of the manual steps required with standard phoropters. However, in contrast, the results will be significantly improved and more precise than today's outcomes.

The system 100 enables clinicians to more successfully detect, diagnose, and treat retinal diseases—such as retinitis pigmentosa, glaucoma, diabetic retinopathy, and macular degeneration-that cause blindness. The patient can obtain better vision correction outcomes, especially through the use of custom contact lenses or custom laser refractive surgery. The information obtained and stored in computer 110 can be used to produce the custom contact lenses and for laser refractive surgery or other custom vision correction procedure or technique.

The system 100 provides a system with reduced size requirements and the system can be constructed using many off-the-shelf, commercial components, which enables the system to be affordable and suitable for clinical environments. The size and weight enable the system to be deployed in a clinician's office setting (nominal footprint=25 inch×44 inch (63 cm×112 cm), weight 110 pounds (50 kg)).

Figure 2:
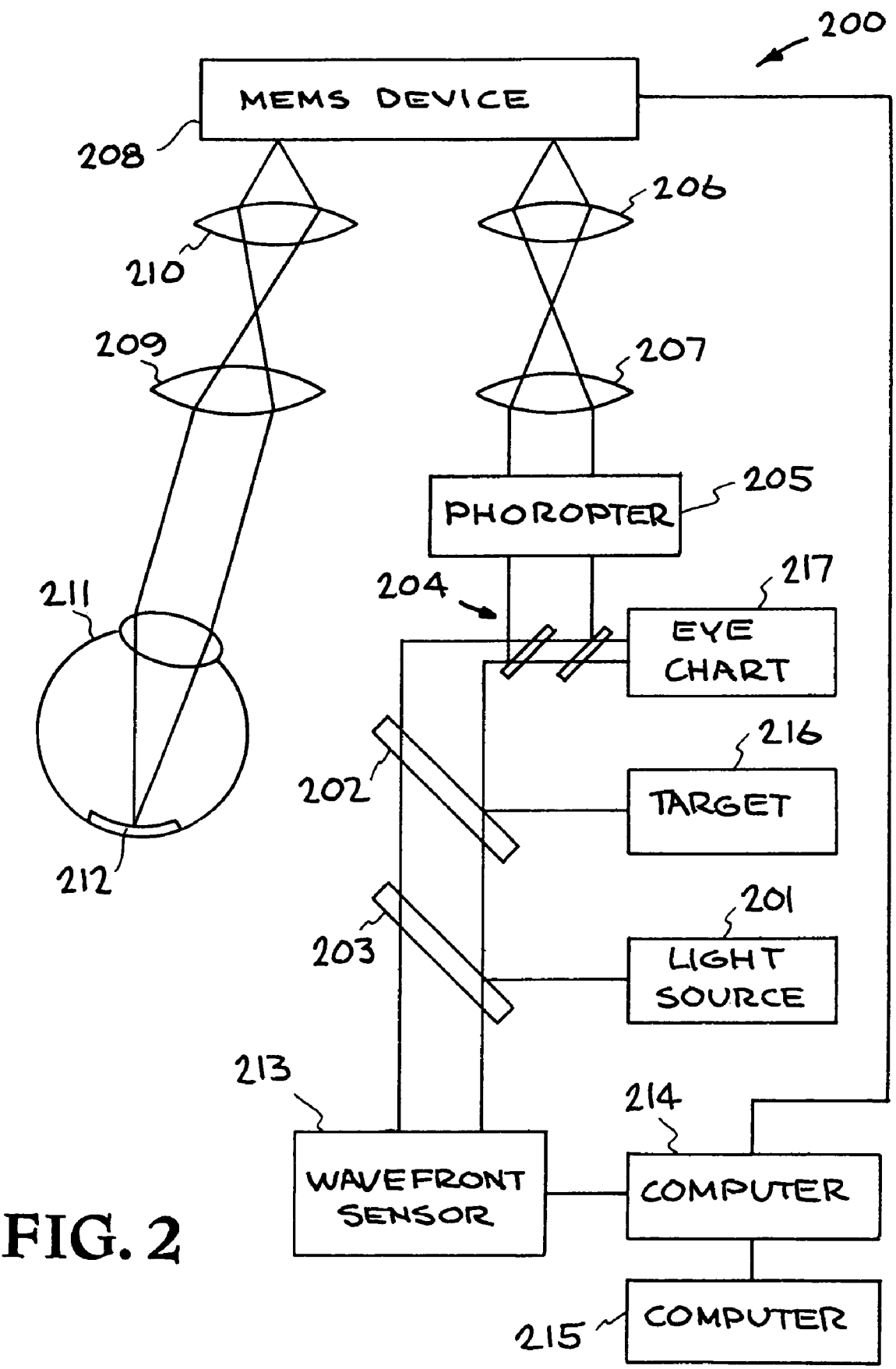
FIG. 2 illustrates another embodiment of a system constructed in accordance with the present invention.

Referring now to FIG. 2, another embodiment of a system constructed in accordance with the present invention is illustrated. The system is designated generally by the reference numeral 200. The system 200 comprises a number of operatively connected elements. The elements shown in FIG. 2 include light source (201), beam splitters (202 & 203), dog-leg (204), phoropter (205), telescopic lens (206 & 207), MEMS device (208), telescopic lens (209 & 210), eye (211), retina (212), wavefront sensor (Hartmann-Shack type) (213), computer (214), additional computer (215), focusing target (216), and visual stimulus, such as an eye chart (217).

Now that the various elements of the system 200 have been identified and described, the operation of the system 200 will be considered. Light is introduced through the light source 201. Light passes through the beam splitters 202 and 103, dog-leg 204, phoropter 205, telescopic lens 206 and 207, and then is reflected off the MEMS device 208 that is used for phase compensation. Another set of telescopic lens 209 and 210 direct the light through the eye 211 and creates an image on the retina 212. The wavefront sensor 213 is of the Hartmann-Shack type. A computer 214 is used to provide use the information from the sensor to adjust the MEMS device 208 based on the information collected by wavefront sensor 213. The items (beam splitters 202 and 203, computer 214, laser 201, and wavefront sensor 213) are all part of a commercial module currently marketed by Wavefront Sciences Inc. The additional computer 215 is used to interface with computer 214 and perform more precise and sensitive information for the MEMS device 208. A focusing target 216 is also present. A visual stimulus, such as an eye chart 217, is shown.

Figure 3:
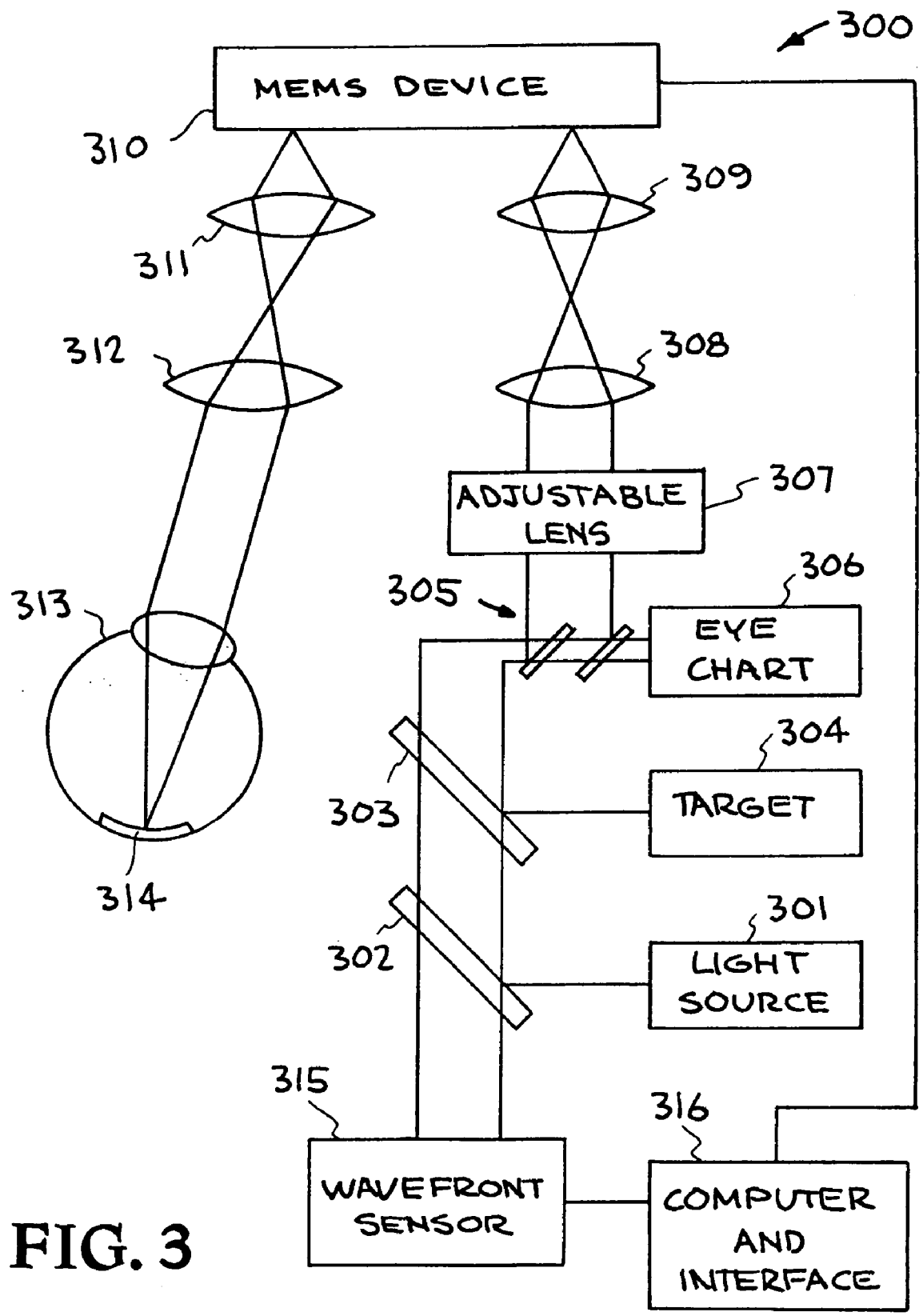
FIG. 3 illustrates another embodiment of a system constructed in accordance with the present invention.

Referring again to the drawings, and in particular to FIG. 3, another embodiment of a system constructed in accordance with the present invention for improving the vision and resolution of retinal images is illustrated. The system is designated generally by the reference numeral 300. The system 300 will enable clinicians to perform detailed vision assessments, apply the appropriate higher-order optical corrections, and then immediately present corrected images to their patients for confirmation.

The system 300 improves a patient's vision by directing a beam of light to the patient's retina 314. The system 300 comprises a number of operatively connected elements. The operative elements and components shown in FIG. 3 include light source 301, beam splitter 302, beam splitter 303, target 304, flip-in mirror or beam splitter 305, adjustable lens 307, telescopic lens 308, telescopic lens 309, MEMS corrector 310, telescopic lens 311, telescopic lens 312, eye 313, retina 314, wavefront sensor 315, and computer and interface 316.

The light source 301 for example can be a laser, a light emitting diode, or a super-luminescent diode available from Wavefront Sciences, Inc., 14810 Central Ave. SE, Albuquerque, N.Mex. 87123. The beam splitters 302 and 303 for example can be beam splitters available from Wavefront Sciences, Inc., 14810 Central Ave. SE, Albuquerque, N.Mex. 87123. The telescopic lens 308, 309, 311, and 312 for example can be commercially available telescopic lenses. The adjustable lens 307 can be for example a phoropter available from Reichert Inc., 3374 Walden Avenue Depew, N.Y. 14043. The MEMS corrector 310 for example can be a MEMS deformable mirror available from Boston Micromachines Corporation, 308 Water Street, Watertown, Mass. 02472. The wavefront sensor 315 for example can be a wavefront sensor available from Wavefront Sciences, Inc., 14810 Central Ave. SE, Albuquerque, N.Mex. 87123. The chart 306 for example can be an "eye chart" or "other means for testing the eye." The computer and interface 316 for example can be a "general purpose computer system."

Now that the various elements of the system 300 have been identified and described, the operation of the system 300 will be considered. Light is generated and introduced into the system by the light source 301. The light passes through beam splitter 302, beam splitter 303, flip-in mirror or beamsplitter 305, adjustable lens 307, telescopic lens 308, and telescopic lens 309, to MEMS corrector 310. The light passes from MEMS corrector 310 through telescopic lens 311, and telescopic lens 312, to the eye 313 and retina 314.

The light creates an image on the retina 314. The return light with the image passes from retina 314 through telescopic lens 312 and telescopic lens 311 to the MEMS corrector 310. The return light passes from the MEMS corrector 310 through telescopic lens 309, and telescopic lens 308, adjustable lens 307, flip-in mirror or beamsplitter 305, beam splitter 303, and beam splitter 302, to the wavefront sensor 315. The return light signal from the wavefront sensor 315 is directed to the computer and interface 316. The computer and interface 316 is connected to the MEMS corrector 303. The return light also passes from the MEMS corrector 310 through telescopic lens 309, telescopic lens 308, adjustable lens 307, and flip-in mirror or beamsplitter 305, to the chart 306.

The corrector 310 will apply the appropriate correction, automatically calculated by the wavefront sensor 315 and computer and interface 316. This information is combined with the response from the patient, so that the clinician and patient can attain the best correction and compensate for high-order aberrations.

The patient is instructed to look at the focusing target 304. The light beam is then introduced into the patient's eye 313 by the laser 301 and creates an image on the retina 314. The wavefront sensor 315 sends information to the computer and interface 316, indicating how to adjust the MEMS wavefront corrector 310.

The system 300 can be operated in a closed-loop mode. Wavefront aberrations are sensed and adjustments are made using the wavefront corrector 315 until the error in wave aberration reaches an asymptotic value as measured by the wavefront sensor 315.

The system 300 can also be used in an open-loop mode. In this state, aberrations are sensed and a single adjustment is made to the corrector to compensate for the measured aberrations. Further adjustments are made based on the subjective response of the patient. The subjective response, coupled with the objective response, insures that the proper correction for higher-order aberrations can be determined quickly. It will also meet the patient's psychophysical demands. That is, the patient will be able to confirm or ask for adjustments based on his/her interpretation of the images viewed.

The flip-in mirror 305 is used in open-loop mode. It is adjusted so that the patient is exposed to a visual stimulus, such as the chart 306. Optionally, if a beam splitter 305 is installed, the patient will be able to see the visual stimulus while the correction is being done. The patient now has the ability to see the objectively determined correction in real time. The clinician is able to obtain the subjective response of the patient. If necessary, the clinician can use the computer and interface 316 to make additional corrections to the MEMS wavefront corrector 310 based on the response of the patient alone.

Patients will have nearly the same experience as they have today. They will view a visual scene (e.g., an eye chart) and asked to comment on whether the scene appears clearer. The clinicians' experience will also be similar, except they will not need to perform many of the manual steps required with standard phoropters. However, in contrast, the results will be significantly improved and more precise than today's outcomes.

The system 300 enables clinicians to more successfully detect, diagnose, and treat retinal diseases—such as retinitis pigmentosa, glaucoma, diabetic retinopathy, and macular degeneration that cause blindness. The patient can obtain better vision correction outcomes, especially through the use of custom contact lenses or custom laser refractive surgery. The information obtained and stored in computer 310 can be used to produce the custom contact lenses and for laser refractive surgery.

The system 300 provides a system with reduce size requirements and the system can be constructed using many off-the-shelf, commercial components, which enables the system to be affordable and suitable for clinical environments. The size and weight enable the system to be deployed in a clinician's office setting (nominal footprint=25 inch×44 inch (63 cm×112 cm), weight 110 pounds (50 kg)).

Figure 4:
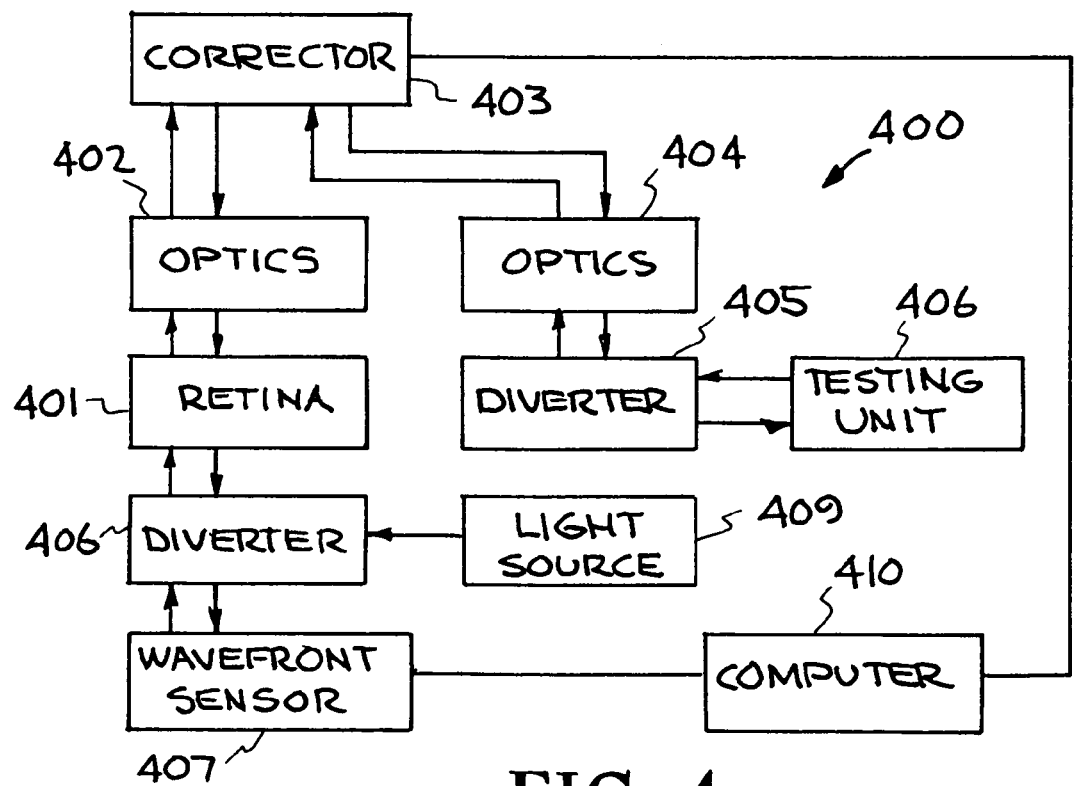
FIG. 4 illustrates another embodiment of a system constructed in accordance with the present invention.

Referring again to the drawings, and in particular to FIG. 4, another embodiment of a system constructed in accordance with the present invention for improving the vision and resolution of retinal images is illustrated. The system is designated generally by the reference numeral 400. The system 400 will enable clinicians to perform detailed vision assessments, apply the appropriate higher-order optical corrections, and then immediately present corrected images to their patients for confirmation. The system 400 improves a patient's vision by directing a beam of light to the patient's retina 401. The system 400 comprises a number of operatively connected elements. The elements shown in FIG. 4 include optics 402, corrector 403, optics 404, diverter 405, diverter 406, wavefront sensor 407, testing unit 408, light source 409, and computer 410.

The light source 409 for example can be a laser, a light emitting diode, or a super-luminescent diode available from Wavefront Sciences, Inc., 14810 Central Ave. SE, Albuquerque, N.Mex. 87123. The diverters 405 and 406 for example can be "beam splitters available from Wavefront Sciences, Inc., 14810 Central Ave. SE, Albuquerque, N.Mex. 87123," "dog-legs," "flip in mirrors," or other "means for diverting light." The optics 402 and 404 for example can be a "telescopic lens," an "adjustable lens," a "phoropter available from Reichert Inc., 3374 Walden Avenue Depew, N.Y. 14043" or a combination of the foregoing. The corrector 403 for example can be a "deformable mirror," a "MEMS device," a "liquid crystal spatial light modulator," or a "MEMS deformable mirror available from Boston Micromachines Corporation, 108 Water Street, Watertown, Mass. 02472." The wavefront sensor 107 for example can be a "Hartmann-Shack type wavefront sensor," a "Hartmann-Shack sensor as described in WO 02/34126, WO 01/58339, WO 02/46801, U.S. Pat. No. 6,382,793, or WO 02/24060, which are incorporated herein by reference)," or a "wavefront sensor available from Wavefront Sciences, Inc., 14810 Central Ave. SE, Albuquerque, N.Mex. 87123." The testing unit 408 for example can be an "eye chart" or "other means for testing the eye." The computer 410 for example can be a "general purpose computer."

Now that the various elements of the system 400 have been identified and described, the operation of the system 400 will be considered. Light is generated and introduced into the system by the light source 409. The light passes through diverter 406 to the retina 401. The light creates an image on the retina 401. The return light with the image passes from retina 401 through the diverter 406, to the wavefront sensor 409. The return light signal from the wavefront sensor 409 is directed to the computer 410. The computer 410 is connected to the corrector 403. The corrector 403 will apply the appropriate correction, automatically calculated by the wavefront sensor 407 and computer 410. Subsequently, the light from the testing unit 408 passes from the diverter 405 through optics 404 to the corrector 403 and optics 402 to the retina 401.

The response from the patient to the image from the testing unit can be used along with the correction automatically calculated by the wavefront sensor, so that the clinician and patient can attain the best correction and compensate for high-order aberrations.

Patients will have nearly the same experience as they have today. They will view a visual scene (e.g., an eye chart) and asked to comment on whether the scene appears clearer. The clinicians' experience will also be similar, except they will not need to perform many of the manual steps required with standard phoropters. However, in contrast, the results will be significantly improved and more precise than today's outcomes.

The system 400 enables clinicians to more successfully detect, diagnose, and treat retinal diseases—such as retinitis pigmentosa, glaucoma, diabetic retinopathy, and macular degeneration-that cause blindness. The patient can obtain better vision correction outcomes, especially through the use of custom contact lenses or custom laser refractive surgery. The information obtained and stored in computer 410 can be used to produce the custom contact lenses and for laser refractive surgery or other custom vision correction procedure or technique.

The system 400 provides a system with reduced size requirements and the system can be constructed using many off-the-shelf, commercial components, which enables the system to be affordable and suitable for clinical environments. The size and weight enable the system to be deployed in a clinician's office setting (nominal footprint=25 inch×44 inch (63 cm×112 cm), weight 110 pounds (50 kg)).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for improving vision by correcting for higher order aberrations utilizing a patient's retina, comprising:
   a laser for producing a laser beam of light,
   a corrector,
   a wavefront sensor,
   a testing unit,
   optic means for directing said laser beam of light to said corrector, to said retina, from said retina to said wavefront sensor, and to said testing unit, wherein said optic means includes an adjustable lens, and
   a computer operatively connected to said wavefront sensor and said corrector.

2. The apparatus for improving vision of claim 1 wherein said corrector comprises a microelectromechanical system corrector.

3. The apparatus for improving vision of claim 1 wherein said corrector comprises a deformable mirror.

4. The apparatus for improving vision of claim 1 wherein said corrector comprises a liquid crystal spatial light modulator.

5. The apparatus for improving vision of claim 1 wherein said corrector comprises a microelectromechanical system deformable mirror.

6. The apparatus for improving vision of claim 1 wherein said testing unit includes an eye chart.

7. The apparatus for improving vision of claim 1 wherein said testing unit includes a video projector.

8. The apparatus for improving vision of claim 1 wherein said testing unit includes a video monitor.

9. The apparatus for improving vision of claim 1 wherein said adjustable lens is a phoropter.

10. The apparatus for improving vision of claim 1 wherein said optic means includes a flip-in mirror operatively connected to said testing unit.

11. The apparatus for improving vision of claim 1 wherein said optic means includes a beam splitter operatively connected to said testing unit.

12. The apparatus for improving vision of claim 1 wherein said optic means includes a beam splitter operatively connected to said laser.

13. The apparatus for improving vision of claim 1 including a target.

14. The apparatus for improving vision of claim 13 wherein said target is a focusing target.

15. The apparatus for improving vision of claim 1 including a diverter means for diverting said laser beam of light to said testing unit.

16. The apparatus for improving vision of claim 15 wherein said diverter means is a flip-in mirror.

17. The apparatus for improving vision of claim 15 wherein said diverter means is a beam splitter.

18. The apparatus for improving vision of claim 1 wherein said wavefront sensor comprises a Hartmann-Shack type wavefront sensor.

19. A method of improving vision by correcting for higher order aberrations utilizing a patient's retina, comprising the steps of:
   producing a laser beam of light utilizing a laser
   directing said laser beam of light to an adjustable lens,
   directing said laser beam of light to a corrector,
   directing said laser beam of light from said corrector to said retina and producing a return laser beam of light,
   directing said return laser beam of light to said corrector, to a wavefront sensor, and to a testing unit.

20. The method of improving vision of claim 19 including the step of having said patient focus on a target.

21. The method of improving vision of claim 19 wherein said wavefront sensor produces information and including the step of capturing said information produced by said wavefront sensor.

22. The method of improving vision of claim 21 including the step of using said information produced by said wavefront sensor to improve said patient's vision.

23. The method of improving vision of claim 22 wherein said step of using said information produced by said wavefront sensor to improve said patient's vision comprises producing custom contact lenses.

24. The method of improving vision of claim 22 wherein said step of using said information produced by said wavefront sensor to improve said patient's vision comprises custom ophthalmologic surgery.

25. The method of improving vision of claim 22 wherein said step of using said information produced by said wavefront sensor to improve said patient's vision comprises custom intra-ocular implants.

* * * * *